(12) United States Patent
Bro et al.

(10) Patent No.: US 7,393,669 B2
(45) Date of Patent: Jul. 1, 2008

(54) METABOLICALLY ENGINEERED MICRO-ORGANISMS HAVING IMPROVED GALACTOSE UPTAKE

(75) Inventors: Christoffer Bro, Gentofte (DK); Birgitte Regenberg, Copenhagen (DK); Jens Nielsen, Charlottenlund (DK)

(73) Assignee: Fluxome Sciences A/S, Lyngby (DK)

( * ) Notice: Subject to any disclaimer, the term of this patent is extended or adjusted under 35 U.S.C. 154(b) by 555 days.

(21) Appl. No.: 10/613,219

(22) Filed: Jul. 7, 2003

(65) Prior Publication Data

US 2005/0009135 A1    Jan. 13, 2005

(51) Int. Cl.
*C12P 7/56* (2006.01)
*C12P 7/48* (2006.01)
*C12P 7/06* (2006.01)
*C12N 1/19* (2006.01)

(52) U.S. Cl. ................ 435/139; 435/144; 435/161; 435/254.21

(58) Field of Classification Search ............... None
See application file for complete search history.

(56) References Cited

U.S. PATENT DOCUMENTS 6,747,137 B1 * 6/2004 Weinstock et al. ......... 536/23.1

OTHER PUBLICATIONS

Ostergaard, et al, Increasing galactose consumption by *Saccharomyces cerevisiae* through metabolic engineering of the GAL gene regulatory network, Nature Biotechnology 18:1283-1286, 2000.*
Oh D and Hopper JE, Transcription of a Yeast Phosphoglucomutase Isozyme Gene is Galactose Inducible and Glucose Repressible, Molecular and Cellular Biology 10(4):1415-1422, 1990.*
Hofmann, M., et al. Characterization of the essential yeast gene encoding N-acetylglucosamine-phosphate mutase. Eur. J. Biochem. 221:741-747, 1994.*
Hoffmann, B., et al. Development and metabolic regulation of the phosphoglucomutase-encoding gene, pgmB, of *Aspergillus nidulans*. Mol. Gen. Genet. 262:1001-1011, 2000.*
Bergmeyer et al "Samples, reagents, assessment of results," *Methods of enzymatic analysis* 2 (2): 278-9, 326-7 (1983).
Bro et al "Metabolic engineering of the galactose utilization pathway in *Saccharomyces cerevisiae* using DNA arrays," 3rd *International Conference on Systems Biology* Kurolinska Institutet, Sockholm Sweden (Dec. 13-15, 2002).
Bro et al "The Impact of DNA arrays on Metabolic Engineering," *Esbes 4 Symposium* Delft University of Technology, The Netherlands (Aug. 28-31, 2002).
Daugherty et al "Purification and Properties of Phosphoglucomutase from Fleischmann's Yeast", *Eur. J. Biochem.* 57: 115-128 (1975).
Dijken et al "An interlaboratory comparison of physiological and genetic properties of four *Saccharomyces cerevisiae* strains", *Enzyme and Microbial Technology* 26: 706-714 (2000).

Elsevier et al "Heterodimer formation and activity in the human enzyme glactose-1-phosphate uridylytransferase", *Proc. Natl. Acad. Sci. USA* Genetics 93: 7166-7171 (Jul. 1996).
Frolova et al "Binding of the glucose-dependent Mig 1p repressor to the *GAL1* and *GAL4* promoters in vivo: regulation by glucose and chromatin structure", *Nucleic Acids Research* 27 (5): 1350-1358 (1999).
Ideker et al "Integrated Genomic and Proteomic Analyses of a Systematically Perturbed Metabolic Network", *Science* 292: 929-934 (May 4, 2001).
Johnston "A Model Fungal Gene Regulatory Mechanism: the *GAL* Genes of *Saccharomyces cerevisiae*", *S. cerevisiae Gal Genes* 51 (4): 458-476 (1987).
Johnston et al "Regulation of Carbon and Phosphate Utilization", *The Molecular and Cellular Biology of the Yeast Saccharomyces: Gene Expression* 2, Chapter 5: 193-281 (1992).
Keleher et al "Ssn6-Tup1 Is a General Repressor of Transciption in Yeast", *Cell* 68: 709-719 (Feb. 21, 1992).
Klein et al "Glucose control in *Saccharomyces cerevisiae*: the role of *MIG1* in metabolic functions", *Microbiology* 144: 13-24 (1998).
Lowry et al "Protein Measurement with the Folin Phenol Reagent", *J. Biol. Chem.* 193: 265-275 (1951).
Masuda et al "Phosphoglucomutase Is an in Vivo Lithium Target in Yeast", *The Journal of Biological Chemistry* 276 (41): 37794-37801 (Oct. 12, 2001).
Melcher "Galactose Metabolism in *Saccharomyces cerevisiae*: A Paradigm for Eukaryotic Gene Regulation", *In Yeast Sugar Metabolism: Biochemistry, genetics, biotechnology, and applications* Chapter 14: 235-269.
Mizoguchi et al "Erythrocyte galactokinase assay with high performance liquid chromatography", *Clinica Chimica Acta* 216: 145-151 (1993).
Møller et al "Steady-state and transient-state analyses of aerobic fermentation in *Saccharomyces kluyven*", *FEMS Yeast Research* 2: 233-244 (2002).
Nielsen "Metabolic engineering", *Appl. Microbiol. Biotechnol.* 55: 263-283 (2001).
Oh "Transcription of a Yeast Phosphoglucomutase Isozyme Gene Is Galactose Inducible and Glucose Repressible", *Molecular and Cellular Biology* 10 (4): 1415-1422 (1990).
Ostergaard et al "Increasing glactose consumption by *Saccharomyces cerevisiae* through metabolic engineering of the *GAL* gene regulatory network", *Nature Biotechnology* 18: 1283-1286 (Dec. 2000).
Platt et al "The yeast galactose genetic switch is mediated by the formation of a Gal4p-Gal3p complex", *The EMBO Journal* 17 (14): 4086-4091 (1998).

(Continued)

*Primary Examiner*—Nancy Vogel
(74) *Attorney, Agent, or Firm*—Iver P. Cooper

(57) ABSTRACT

A recombinant prototrophic micro-organism such as a yeast is provided which over-expresses the activity of an enzyme catalysing the conversion of glucose-1 phosphate to glucose-6 phosphate in the galactose uptake and metabolism pathway. Suitably the increased enzyme activity is due to over-expression of the gene PGM2. This produces increased uptake of galactose and increased ethanol production when the organism is grown on a galactose containing medium.

15 Claims, 4 Drawing Sheets

OTHER PUBLICATIONS

Purnelle et al "Analysis of an 11•7 kb DNA Fragment of Chromosome XI Reveals a New tRNA Gene and Four New Open Reading Frames Including a Leucine Zipper Protein and a Homologue to the Yeast Mitochondrial Regulator ABF2", *Yeast* 10: 125-130 (1994).

Treitel et al "Repression by SSN6-TUP1 is directed by MIG1, a repressor/activator protein", *Proc. Natl. Acad. Sci. USA* 92: 3132-3136 (Apr. 1995).

Verduyn et al "Effect of Benzoic Acid on Metabolic Fluxes in Yeasts: A Continuous-Culture Study on the Regulation of Respiration and Alcoholic Fermentation", *Yeast* 8: 501-517 (1992).

Wieczorke et al "Concurrent knock-out of at least 20 transporter genes is required to block uptake of hexoses in *Saccharomyces cerevisiae*", *FEBS Letters* 464: 123-128 (1999).

Zheng et al "The Cysteine-Peptidase Bleomycin Hydrolase Is a Member of the Galactose Regulon in Yeast", *The Journal of Biological Chemistry* 272 (48): 30350-30355 (Nov. 28, 1997).

Zhu et al "Global Analysis of Protein Activities Using Proteome Chips", *Science* 293: 2101-2104.

* cited by examiner

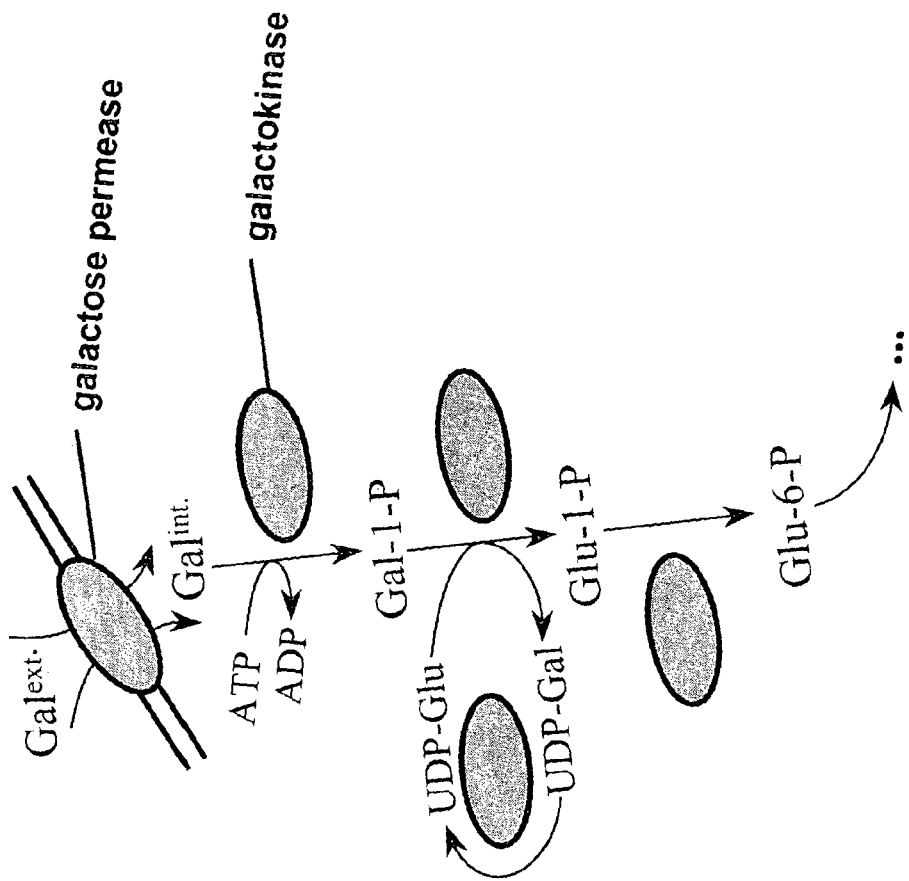
Figure 1 The Leloir pathway for galactose uptake and metabolism

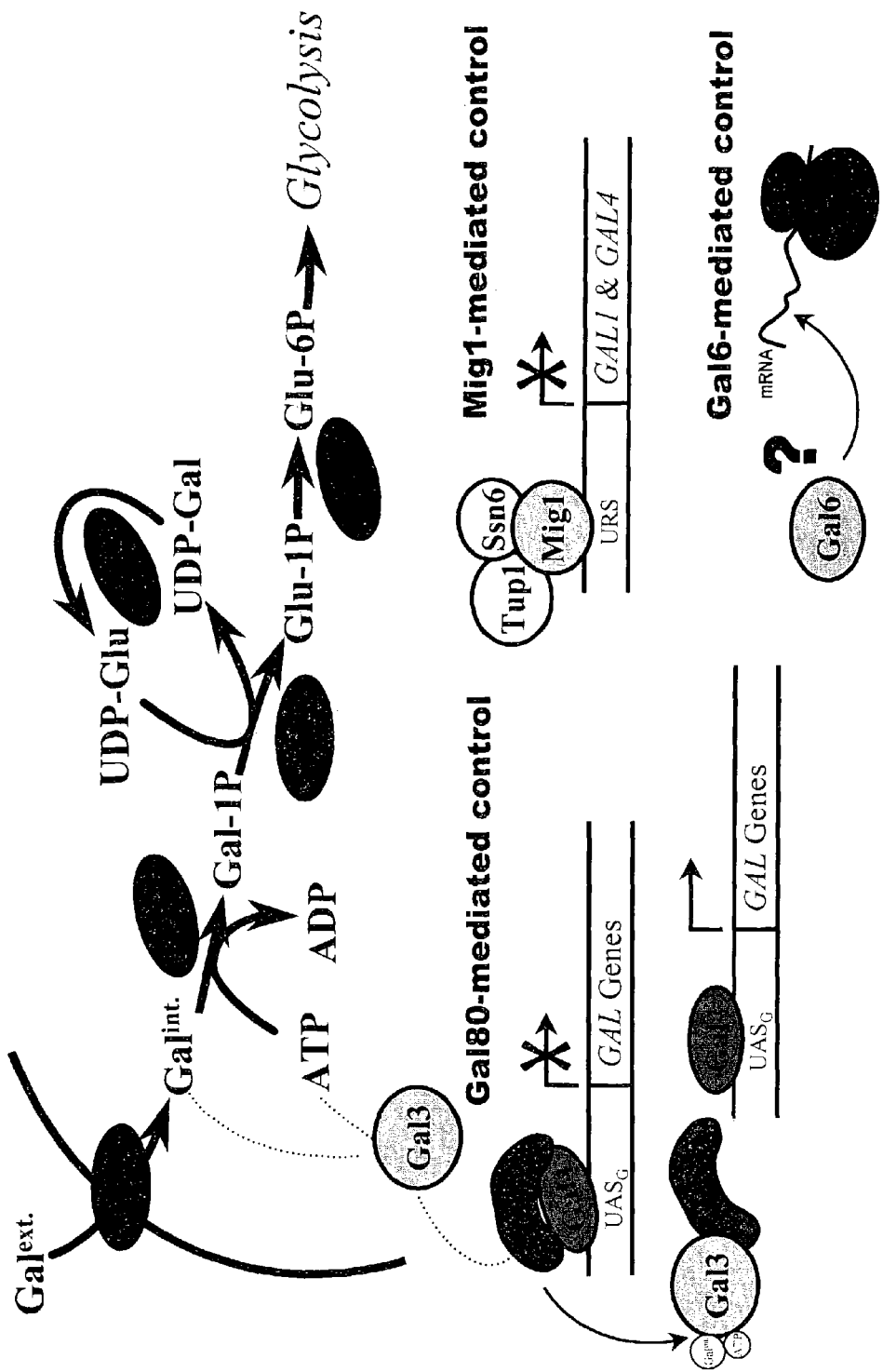
Figure 2 Regulation of the GAL-system in *Saccharomyces cerevisiae*

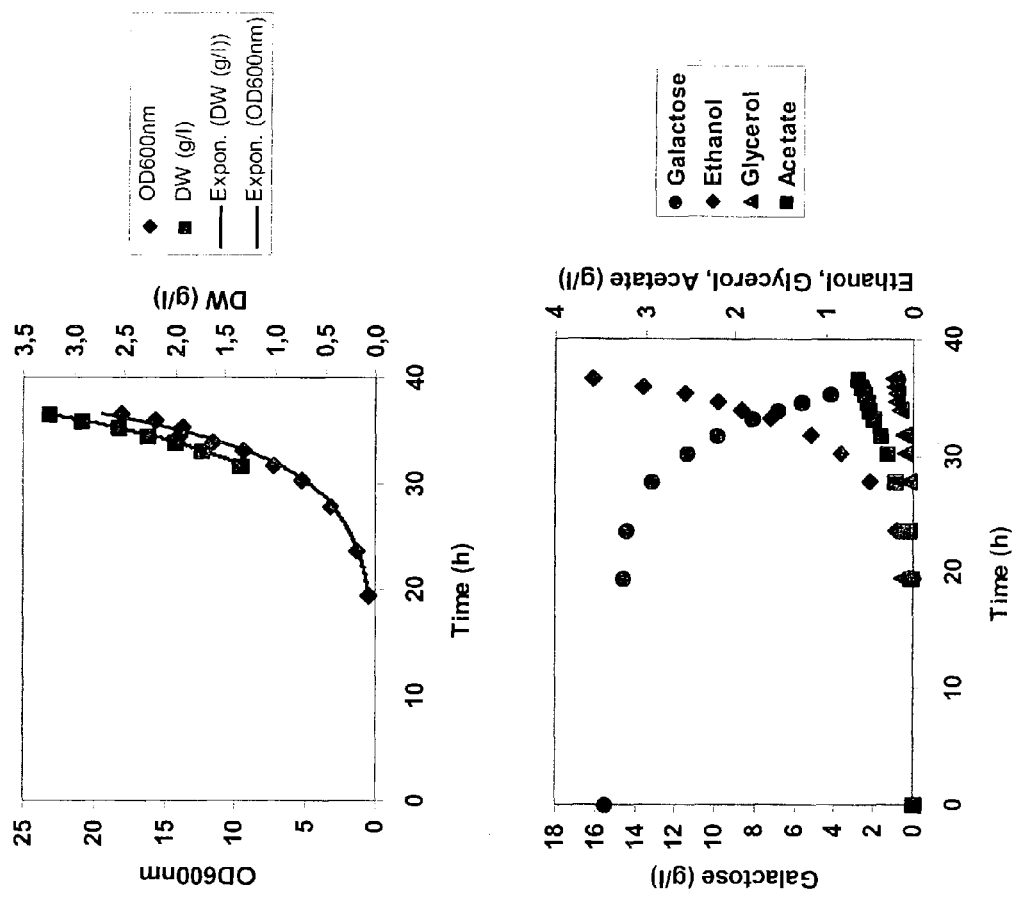

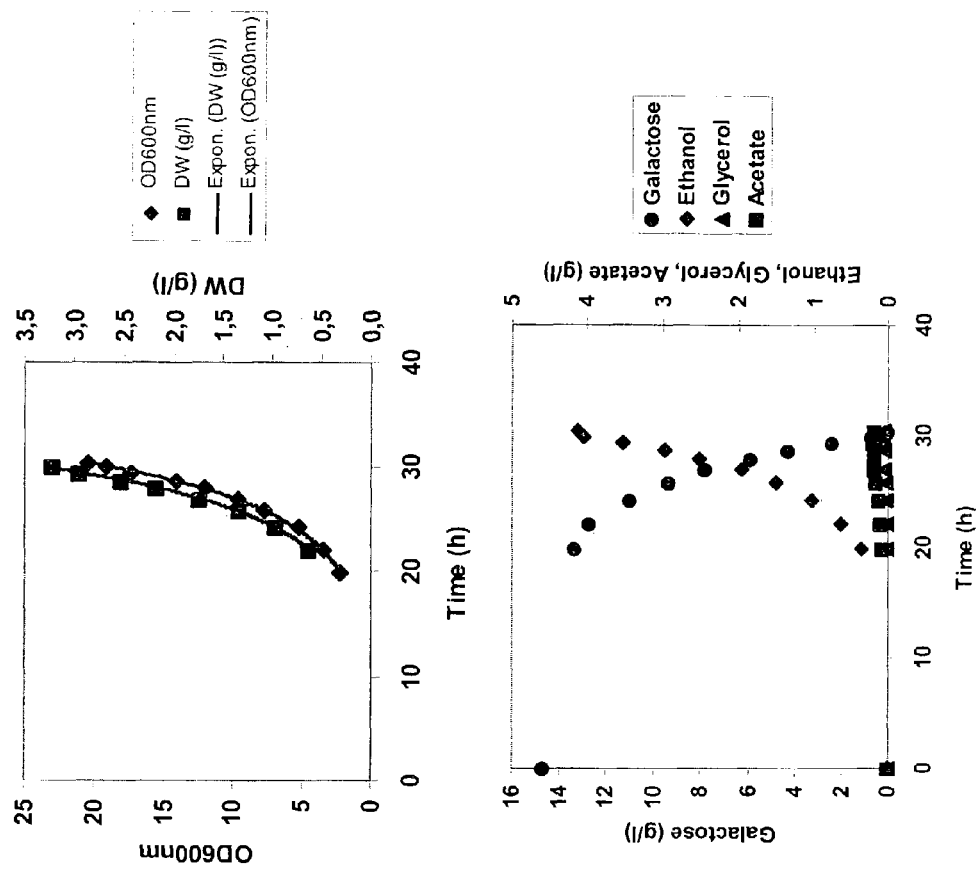
Figure 4 Batch cultivation with strain over-expression PGM2

METABOLICALLY ENGINEERED MICRO-ORGANISMS HAVING IMPROVED GALACTOSE UPTAKE

BACKGROUND OF THE INVENTION

Galactose is an abundant sugar in many different raw materials for industrial fermentation processes. Thus, galactose is one of the sugars present in lactose, the primary sugar of whey. It is also present in raffinose, a sugar present in beet molasses. Furthermore, it represents 3-18% of the sugars present in hemicellulose from various plant sources. Galactose can be metabolized by most micro-organisms. However, the rate of uptake of galactose is for most organisms substantially lower than the uptake of the sugars glucose, fructose and mannose. For exploitation of galactose as a raw material for industrial fermentations in the production of low value added products like ethanol, lactic acid and citric acid the slow uptake rate of galactose represents a fundamental problem.

Within the last decade metabolic engineering has been successfully applied for optimisation of several industrial fermentation processes (Nielsen, 2001). Recombinant DNA techniques have facilitated the ability to genetically modify suitable host systems, and this has resulted in recombinant strains that have reduced by-product formation with a resulting increase in the overall yield of product. For many industrial processes—especially those involving low-value added products—the yield is certainly important, but it is also important to have a high rate of conversion of the substrate into the product. This requires optimisation of the flux through the central carbon metabolism, which has been attempted for glycolysis in *Saccharomyces cerevisiae* (Schaff et al., 1989) and in other micro-organisms. These attempts have, however, largely failed for two major reasons. First, control of flux through central carbon metabolism is often distributed over many enzymes, so an increase in flux requires increased activity of many (or all) enzymes in the pathway. Second, regulation of glycolysis—both at the genetic and at the enzymatic level—is generally believed to be very rigid making it difficult to modulate flux through amplification of individual enzyme activities.

One way to solve these problems may be over expression of many (or all) genes encoding the enzymes in a given pathway. However, this may impose a physiological burden on the cell by draining pools of nucleotides or amino acids, or by slowing down transcriptional or translational efficiency. This may have metabolic consequences in other parts of metabolism, which negatively affects the overall performance of the cell. Furthermore, high levels of all the enzymes in the pathway may lead to significant changes in metabolite levels, which may result in down-regulation of some enzymes.

In fungi the uptake and metabolism of galactose is via the Leloir pathway (see FIG. 1). In this pathway galactose is first transported into the cell by a specific permease. In the next step the sugar is phosphorylated into galactose-1-phosphate, a reaction that is catalyzed by a specific kinase. In the next step of the pathway galactose-1-phosphate reacts with UDP-glucose and forms glucose-1-phosphate and UDP-galactose, a reaction that is catalyzed by galactose-1-phosphate uridylyltransferase. Regeneration of UDP-glucose from UDP-galactose is catalyzed by a separate enzyme involved in the pathway—UDP-glucose 4-epimerase. Glucose-1-phosphate is the end product of the Leloir pathway, but in the further catabolism of galactose this sugar phosphate is further converted into glucose-6-phosphate, which may be further processed via the Embden Meyerhof Parnas pathway or the Pentose Phosphate pathway. The conversion of glucose-1 phosphate to glucose-6 phosphate is catalyzed by the enzyme phosphoglucomutase (PGM). As glucose-1 phosphate is used as precursor for trehalose, glycogen and glucan biosynthesis, PGM also plays a role during metabolism of glucose, but here it catalyzes the conversion of glucose-6 phosphate to glucose-1 phosphate.

The galactose metabolism is subjected to dual control, being induced by galactose and repressed by glucose. Regulation has been extensively studied in the yeast *Saccharomyces cerevisae*, which preferably uses glucose as energy and carbon source over galactose. In this yeast the genes involved in galactose metabolism, often referred to as the GAL genes, are subjected to glucose repression to a much larger extent than other genes controlled by glucose such as the MAL genes and the SUC genes (Johnston and Carlson, 1992; Klein et al., 1998). The structural GAL genes subjected to this dual control are the GAL2 gene, encoding galactose permease, the GAL1 gene, encoding galactokinase, the GAL7 gene, encoding galactose-1-phosphate uridylyltransferase, and the GAL10 gene, encoding UDP-glucose 4-epimerase. Transcription of these structural GAL genes is enhanced 1000-fold after de-repression by glucose and induction by galactose (Melcher, 1997). In *S. cerevisiae* phosphoglucomutase is often referred to as the Gal5 protein, but as there are two isoforms of the enzyme a more correct description of this enzyme is designation of each isoform encoded by the two genes PGM1 and PGM2. Both these genes are not under the same tight control as GAL1, GAL2, GAL7 and GAL10, as their transcription are only increased threefold in the presence of galactose (Oh and Hopper, 1990). This is likely a consequence of the high basic level of expression of the PGM2 gene at non-induced conditions independent of the positive transcriptional activator Gal4 (Oh and Hopper, 1990), which may be due to the role of phosphoglucomutase in the glycogen, trehalose and glucan biosynthesis. In fact phosphoglucomutase is generally believed to be in excess as it can equilibrate the pools of glucose-1 phosphate and glucose-6 phosphate (Zubay, 1988). Furthermore this enzyme has a high affinity for its substrates (Daugherty et al. 1975). For these reasons gene products of PGM1 and PGM2 are generally not believed to exert any degree of flux control in the Leloir pathway, which is consistent with the situation of the glycolysis where no single enzyme has been shown to exert any significant flux control.

The system involved in regulation of the expression of the structural GAL genes is illustrated in FIG. 2. The regulatory GAL gene products comprise Gal3 and Gal4 that are necessary for induction of the GAL genes. The protein Gal4 acts as a transcriptional activator of the GAL genes by binding to specific sequences upstream of the coding region (Johnston, 1987). The GAL80 gene encodes a protein that binds to Gal4 and prevents this protein from activating transcription. Recent in vitro studies strongly indicated that Gal3 interacts with Gal80 and the interaction of Gal3 with Gal80 is believed to relieve the interaction between Gal80 and Gal4 which covers the activating domain of Gal4, and hence, transcriptional activation of the GAL genes is possible (Platt and Reece, 1998). Another regulatory gene recently devoted to the group of GAL genes is the GAL6 gene, which has been shown to be regulated by galactose (Zheng et al., 1997). GAL6 is regulated in similar way as GAL80 and the gene product has a negative impact on expression of the GAL genes, but the actual mechanism of action within the GAL system still remains to be elucidated. Finally, Mig1-mediated glucose repression also imposes control over the GAL system (Johnston and Carlson, 1992). The Mig1 protein takes part in a protein complex with the proteins Ssn6 and Tup1, which binds to the GAL1 promoter and the GAL4 promoter (Keleher et al., 1992; Treitel and Carlson, 1995; Frovola et al., 1999) and hence preventing transcription of these two genes. Repression of the latter gene has a major effect by down-regulation of the whole GAL system.

Ostergaard et al. (2000) report on modulation of the regulatory GAL system for improving the uptake and metabolism of galactose. They constructed and analysed a number of recombinant strains with alteration in the expression of regulatory genes. The best effect was obtained by deleting the three genes MIG1, GAL80 and GAL6 whereby the galactose uptake rate increases 41%. A positive effect was also found by over expression of GAL4 resulting in a 26% increase in the galactose uptake rate. Deletion of GAL6 alone results in a 24% increase in the galactose uptake rate, whereas deletion of MIG1 and GAL80 alone increases the galactose utilisation with 15% (Ostergaard et al., 2000). Based on these findings it was speculated that deletion of negative regulatory genes like MIG1, GAL80 and GAL6 and over expression of the gene GAL4 encoding the positive transcriptional regulator results in an co-ordinated and balanced increased expression of the structural GAL genes GAL1, GAL2, GAL 7 and GAL10 leading to an increased flux through the Leloir pathway.

Masuda et al (2001) investigated the effect of lithium on the metabolism of galactose in *Saccharomyces cerevisiae* and in particular on the phosphoglucomutase activity due to transcription of the PGM2 gene. One of the constructs they used was an auxotrophic (leucine and histidine requiring) strain over expressing PGM2. Such a strain would be unsuitable for commercial use because of its auxotrophic nature and would not be able to grow on minimal media (i.e. media not supplemented to supply the amino acids required by the auxotrophic strain. This strain is used in Masuda et al. only as a basis for comparison in the investigation of the effect of lithium with a view to better understanding the mechanism of the therapeutic effect of lithium in treating manic depressive disorder in humans. PGM2 over expression was used only to demonstrate that this could overcome the suppression of PGM2 activity otherwise produced by lithium stress. No beneficial result relevant to the normal cultivation of *S. cerevisiae* was reported.

In the present invention we applied genome-wide transcription analysis using DNA arrays to identify differently expressed genes in three of the strains with different galactose utilisation capacity studied by Ostergaard et al. (2000). Based on this analysis we identified PGM2 to be an important gene for ensuring a high galactose uptake rate.

BRIEF SUMMARY OF THE INVENTION

The present invention now provides a recombinant, prototrophic micro-organism exhibiting an increased level of galactose uptake rate when cultured on a nutrient source providing galactose, said micro-organism being a yeast or other fungi having the ability to grow on minimal medium and over expressing the activity of an enzyme catalysing the conversion of glucose-1 phosphate to glucose-6 phosphate in the galactose uptake and metabolism pathway compared to a reference micro-organism having a native level of activity of said enzyme and from which the recombinant micro-organism is derived.

Other genetic modifications of a starting non-recombinant strain may be made before, after or simultaneously with the introduction of the modification giving rise to over-expression of the said enzyme activity.

DETAILED DESCRIPTION OF THE INVENTION

Said micro-organism may be a fungi and said enzyme may be a phosphoclugomutase. Specifically the enzyme may be Gal5 and may be encoded by either or both of the genes PGM1 and PGM2.

Preferably, said enzyme activity is expressed in the micro-organism at a level which is at least 1.5 times that of the said reference micro-organism.

The over expression may be brought about by introducing multiple copies of a gene coding for the said enzyme. Alternatively or additionally, a gene coding for the said enzyme may be under the control of a genetic control sequence which has been recombinantly introduced and which is not natively associated with said gene, leading to said over expression of said enzyme activity. Alternatively or additionally there may be present a gene coding for a mutated form of the said enzyme which mutated form has a higher specific activity than the native form of said enzyme of said micro-organism. Specific methodologies for mutating yeast strains to produce over expression of genes by all of these methods are well known in the art.

Preferably, the micro-organism is a yeast. It may be a strain of *Saccharomyces cerevisiae*. More generally the micro-organism may be a species belonging to the genus *Saccharomyces*, e.g. *S. cerevisiae*, *S. kluyveri*, *S. bayanus*, *S. exiguus*, *S. sevazzi*, *S. uvarum*, a species belonging to the genus *Kluyveromyces*, e.g. *K. lactis K. marxianus* var. *marxianus*, *K. thermotolerans*, a species belonging to the genus *Candida*, e.g. *C. utilis C. tropicalis*, a species belonging to the genus *Pichia*, e.g. *P. stipidis*, *P. pastoris*, *P. sorbitophila*, or other yeast species, e.g. *Debaromyces hansenii*, *Hansenula polymorpha*, *Yarrowia lipolytica*, *Zygosaccharomyces rouxii* or *Schizosaccharomyces pombe*.

Concerning other fungal micro-organisms, a non-exhaustive list of suitable micro-organisms will include the following:

*Aspergillus niger*, *Aspergillus awamori*, *Aspergillus oryzae*, *Aspergillus nidulans*, *Penicillium chrysogenum*, *Rhizopus oryzae*.

The micro-organism preferably exhibits an increase of the maximum specific galactose uptake rate of at least 10%, more preferably at least 20%, for instance at least 40%, in comparison to a said reference micro-organism.

Preferably, the micro-organism exhibits an increase of said enzyme activity of at least 2 fold, more preferably at least 5 fold, more preferably at least 10 fold, more preferably at least 20 fold, more preferably 100 fold, in comparison to a said reference micro-organism.

Preferably, the micro-organism exhibits an increased maximum specific ethanol production rate compared to said reference micro-organism, e.g. said ethanol production is increased by at least a factor of 1.1, more preferably by at least a factor of 1.5.

BRIEF DESCRIPTION OF THE ACCOMPANYING DRAWINGS

FIG. 1 shows an overview of the Leloir pathway.

FIG. 2 shows the regulation of the GAL system in *S. cerevisiae*.

FIG. 3 shows the result of batch cultivation of the strain SO7 in Example 2 below.

FIG. 4 shows the result of batch cultivation of the PGM2 strain in Example 6 below.

As described below, we have genetically engineered a strain of *S. cerevisiae* to over express the PGM2 gene by transformation with a multicopy plasmid vector containing the PGM2 gene under the control of a strong promoter to obtain a non-auxotrophic (prototrophic) strain exhibiting increased PGM enzyme activity whilst being able to grow on minimal medium (and specifically being able to grow in the absence of added leucine and histidine). It is found that surprisingly this strain has increased flux through the galactose pathway when cultured with a supply of galactose, leading to increased uptake of galactose and increased ethanol production.

The invention will be further described with reference to the following Examples which are non-limiting and presented for illustration.

EXAMPLE 1

Construction of Yeast Strains

All *S. cerevisiae* strains used were generated from the CEN.PK113-7D (MATa) wild type strain (van Dijken et al. 2000). SO7 containing the 2μ high-copy vector pBM959 with GAL4 behind its native promoter and URA3 as marker and SO16 (gal80, mig1, gal6) were constructed by Ostergaard and co-workers (Ostergaard et al., 2000). The PGM2 strain overexpressing PGM2 was constructed by transforming CEN.PK113-5D (ura3) with the 2μ high-copy vector pPGM2 (Masuda et al., 2001) containing PGM2 behind the PMA1 gene promoter and URA3. Strains were stored at −80° C. in 20% (v/v) glycerol. These frozen stocks were used for obtaining single colonies on plates with a selective minimal medium for inoculation of precultures.

EXAMPLE 2

Batch Cultivations of WT, SO7 and SO16

The *S. cerevisiae* strains either overexpressing GAL4 (SO7) or deleted in GAL6, GAL80 and MIG1 (SO16) and the corresponding reference strain CEN.PK113-7D (WT) were examined under controlled conditions in aerobic batch cultivations on a minimal media with a start concentration of 15 g/l galactose. All the strains were prototrophic thereby avoiding addition of various amino acids that could affect transcription of amino acid related genes. Cultivations of all strain were done in triplicates and samples for DNA arrays were harvested at a residual galactose concentration of 7.5±2.0 g/l.

The batch cultivations were carried out in well-controlled laboratory fermenters with a working volume of 2 or 4 litres. A defined medium (Verduyn et al., 1992) was used, which contained per litre: 15 g galactose; 5.0 g $(NH_4)_2SO_4$; 3.0 g $KH_2PO_4$; 0.5 g $MgSO_4, 7H_2O$; and trace metals and vitamins as described by Verduyn et al. (1992). 50 μl/L antifoam (Sigma A-8436) was added to avoid foaming. Galactose was autoclaved separately from the mineral medium and afterwards added to the fermenter together with a sterile filtrated solution containing the vitamins.

Precultures were grown at 30° C. and 150 rpm in cotton-stopped, 500 ml Erlenmeyer flasks with baffles containing each 100 ml of a media of pH 6.5 similar to that in the fermenters, but containing different concentrations of galactose (20 g/L), $(NH_4)_2SO_4$ (7.5 g/L) and $KH_2PO_4$ (14 g/L). Precultures were inoculated directly from frozen stocks, and grown at 30° C. on selective media. Exponential phase precultures were used to inoculate to a start concentration of 1 mg CDW/L.

Cultivations were carried out at 30° C. with a stirrer speed of 800 rpm and were aerated with air at a flow rate of 1 litre per litre staring volume per minute. The concentration of dissolved oxygen was measured with a Mettler Toledo polarographic electrode and remained above 70%. pH was kept at 5.0 by automatic addition of 4 M KOH. The bioreactors were fitted with cooled condensers, and the off-gas was led to a gas analyser (INNOVA, Denmark) to measure the content of $CO_2$.

The concentration of biomass in batch fermentations was determined on a dry weight basis by filtering a known volume of culture through a pre-weighed 0.45 μm nitrocellulose filter (Gelman Sciences, Ann Arbor, Mich.). The filter was washed with distilled water, dried in a microwave oven at 150 W for 15 minutes and finally weighed to determine its increase in dry weight.

Culture samples for determination of galactose, ethanol, glycerol, acetate, pyruvate and succinate concentrations were filtered through a 0.45 μm cellulose acetate filter (Osmonics) immediately after sampling, and the filtrate was frozen at −20° C. until further analysis. The concentrations of the metabolites were determined by high-pressure liquid chromatography on an Aminex HPX-87Hm column (Bio-Rad) kept at 65° C. and eluted at 0.6 ml per minute with 5 mM $H_2SO_4$. Acetate and pyruvate were detected spectrophotometrically by a Waters 486 Turnable Absobance Detector at 210 nm. Galactose, ethanol, glycerol and succinate were detected refractometrically by a Waters 410 Differential Refractometer.

Results from the batch cultivation with the strain SO7 are shown in FIG. 3 and overall results from batch cultivations of all three strains are shown in the table below.

|  | WT | SO7 | SO16 |
| --- | --- | --- | --- |
| Specific growth rate ($h^{-1}$) | 0.17 ± 0.01 | 0.18 ± 0.01 | 0.18 ± 0.00 |
| Specific galactose uptake rate (g galactose/g DW/h) | 0.60 ± 0.03 | 0.80 ± 0.04 | 0.84 ± 0.02 |
| Specific ethanol production rate (g ethanol/g DW/h) | 0.11 ± 0.01 | 0.19 ± 0.02 | 0.22 ± 0.01 |
| Yield of biomass on galactose (g DW/g galactose) | 0.22 ± 0.01 | 0.22 ± 0.01 | 0.22 ± 0.01 |

Data is given as the average of three similar independent cultivations ± the standard deviation.

EXAMPLE 3

Genome-Wide Transcription Analysis

Oligonucleotide microarrays from Affymetrix containing sequences for all know ORFs in *S. cerevisiae* were used for genome-wide expression analysis during batch cultivations with the strains SO7, SO16 and WT.

To find genes, which had changed expression in at least one of the two mutants an ANOVA analysis was performed on the 5963 probe sets representing ORFs in *S. cerevisiae* that were called present on at least one array. Only 24 ORFs showed a significantly changed expression in at least one of the two mutants when using a global likelihood of getting 1 false positive (cutoff at $P=1.68 \cdot 10^{-4}$), and most of these ORFs had only changed expression in the GAL4 overexpression strain. The 30 best scoring genes in the ANOVA test are shown in the table below.

|  |  |  | Fold change[a] | | |
| --- | --- | --- | --- | --- | --- |
| ORF |  | Function | SO7 | SO16 | P-value[b] |
| YGL157W |  | Unknown | 3.7 | −1.5 | 3.53E−08 |
| YEL021W | URA3 | Pyrimidine biosynthesis | 5.2 | −1.2 | 5.66E−07 |
| YPL248C | GAL4 | Galactose regulation | 23 | 1.3 | 5.95E−07 |
| YBR298C | MAL31 | Maltose metabolism | −1.4 | 1.1 | 3.85E−06 |
| YML051W | GAL80 | Galactose regulation | 1.3 | −2.1 | 7.90E−06 |
| YJL056C | ZAP1 | Transcriptional regulation | 2.3 | 1.1 | 1.31E−05 |
| YLR035C | MLH2 | DNA repair | 3.1 | −1.5 | 2.60E−05 |
| YBR093C | PHO5 | Phosphate metabolism | 32 | 1.0 | 3.11E−05 |
| YIL057C |  | Unknown | −1.2 | 1.8 | 3.77E−05 |
| YGL130W | CEG1 | mRNA capping | 2.1 | 1.0 | 5.54E−05 |
| YOL143C | RIB4 | Riboflavin biosynthesis | 1.7 | 1.2 | 5.76E−05 |
| YKL031W |  | Unknown | 9.4 | 1.9 | 6.04E−05 |
| YLR286C | CTS1 | Cell wall biogenesis | −1.4 | 1.1 | 7.30E−05 |
| YNL239W | GAL6 | Galactose rebgulation | 2.0 | −150 | 7.65E−05 |
| YGR022C |  | Unknown | 10 | 1.0 | 9.68E−05 |
| YEL069C | HXT13 |  |  |  |  |
| YDL245C | HXT15 |  |  |  |  |
| YJR158W | HXT16 |  |  |  |  |
| YNR072W | HXT17 | Hexose transporters | 1.0 | 3.2 | 9.95E−05 |
| YBR299W | MAL32 |  |  |  |  |
| YGR292W | MAL12 | Maltose metabolism | −2.3 | 1.2 | 1.07E−04 |
| YOL126C | MDH2 | Gluconeogenesis | 2.1 | −1.2 | 1.13E−04 |
| YFL011W | HXT10 | Hexose transporter | 2.7 | 1.7 | 1.19E−04 |
| YMR305C | SCW10 | Mating | −1.6 | −1.2 | 1.37E−04 |
| YKL216W | URA1 | Pyrimidine biosynthesis | 1.7 | 1.1 | 1.42E−04 |
| YDR520C |  | Unknown | 1.7 | 1.1 | 1.42E−04 |
| YGL035C | MIG1 | Glucose repression | −1.3 | −17 | 1.46E−04 |
| YPL187W | MFα1 | Mating | −2.1 | −2.1 | 1.48E−04 |
| YMR199W | CLN1 | Cell cycle | −1.7 | −1.1 | 1.63E−04 |
| YJR159W | SOR1 | Fructose metabolism |  |  |  |
| YDL246C |  | Unknown | 2.2 | 1.4 | 1.83E−04 |
| YMR176W | ECM5 | Cell wall biogenesis | 2.1 | 1.1 | 2.04E−04 |
| YOL058W | ARG1 | Arginine biosynthesis | 1.2 | 1.0 | 2.19E−04 |
| YOR378W |  | Unknown | 5.8 | 1.5 | 2.49E−04 |
| YGR249W | MGA1 | Filamentous growth | −3.2 | −2.4 | 2.53E−04 |

[a]Fold change compared to wild type strain.
[b]P-value returned by ANOVA. The lower the value the higher probability of a significant changed expression.

Five of the 24 ORF with changed expression are GAL4, GAL6, GAL80, MIG1 and URA3, which were deleted or over-expressed in one of the two mutants. Of these five ORFs GAL4, GAL6 and GAL80 showed possible changes in the strain were they had not been deleted or over-expressed—a 1.3-, 2.0- and 1.3-fold up-regulation respectively. We expected to see many of the Gal4 activated genes to be up-regulated, but GAL6 is the only gene with a Gal4 binding site in its promoter, which was up-regulated among the 24 significantly changed genes. The hypothetical ORF YIL057C also has a putative Gal4 binding site in its promoter (Ideker et al., 2001), but is down-regulated 2.2 fold in SO7. From the significantly changed genes we could not identify any genes with changed expression in both mutants, which could be new candidates as key enhancers of the flux through the galactose utilisation pathway. Most of the genes with significantly changed expression are likely to be secondary effects of over-expressing GAL4, since many of them has changed expression in SO7 only.

HXT10, which is able to transport galactose (Wieczorke et al. 1999) is up-regulated in both SO7 and SO16 and could be a possible key enhancer, but HXT10 is lowly expressed compared to GAL2. The probe set representing HXT13, HXT15-17 was up-regulated 3.2 fold in SO 16, however, none of these HXT's are able to transport galactose (Wieczorke et al. 1999). The hypothetical ORF YKL031W is up-regulated 9.4 fold in SO7 and 1.9 fold in SO16 compared to the wild type strain. YKL031W is coding a protein of 137 amino acids which binds phosphoinositol 4,5-biphosphate in vitro (Zhu et al., 2001) and contains two predicted transmembrane segments (Purnelle and Skala, 1994), but which has no related proteins.

Surprisingly expression of GAL1, GAL2, GAL7 and GAL10 were not higher in the mutants than the wild type. Apparently they were already expressed at their maximum level in the wild type strain.

EXAMPLE 4

Identification of Target for Metabolic Engineering

The genome-wide transcription analysis of the two mutants did not identify any new gene candidates for being key enhancers of the galactose flux. Nor did it indicate any reason for the mutant's increased galactose uptake rates, such as significantly increased transcription levels of the genes encoding the Gal enzymes. We therefore looked further into the transcription results for the GAL genes, which are the most obvious candidates for key enhancers, and which we had hypothesised would be up-regulated to balanced levels in the two mutants. Results of this analysis are shown in the table below.

|  | Transcription | | |
| --- | --- | --- | --- |
|  | Fold change[a] | | |
| Gene | SO7 | SO16 | P[b] |
| GAL4 | 23 | 1.3 | $6.0 \cdot 10^{-7}$ |
| GAL80 | 1.3 | −2.1 | $7.9 \cdot 10^{-6}$ |
| GAL6 | 2.0 | <−100 | $7.710^{-5}$ |
| PGM2 | 1.7 | 1.3 | $6.1 \cdot 10^{-3}$ |
| GAL7 | 1.0 | 1.1 | 0.17 |
| GAL3 | 1.7 | 1.0 | 0.18 |
| GAL2 | 1.0 | 1.1 | 0.38 |
| GAL10 | 1.0 | 1.1 | 0.46 |
| PGM1 | 1.2 | 1.1 | 0.57 |
| GAL1 | 1.0 | 1.0 | 0.99 |

[a]Fold change compared to wild type strain.
[b]P-value returned by ANOVA. The lower the value the higher probability of a significant changed expression.

Except from GAL4, GAL6, and GAL80, only PGM2, encoding the major isoform of phosphoglucomutase, Gal5, had a high probability of being significantly changed. For the genes encoding the first four enzymes in the galactose utilisation pathway the probability of a changed expression was less than 83% when not even considering multiple testing. Taking multiple testing of the 10 GAL genes into consideration there was a 94% probability of a changed expression of PGM2 in at least one of the two mutant strains. PGM2 expression had only increased 1.7 and 1.3 fold in S07 and S016 respectively, so On the basis of the transcription analysis only PGM2 was identified as a possible new key enhancer gene for increasing the galactose flux.

EXAMPLE 5

Measurement of Enzyme Activities

To verify that concentration of active Gal5 had indeed a higher increased expression and that other Gal enzymes had not, the in vitro enzyme activities of Gal1, Gal7 and Gal5 were measured in cell free extracts from the same cultivations.

Cell free extracts were produced with the help of a Fastprep FP120 instrument (Savant Instruments, New York) as previously described (Møller et al., 2002). In vitro enzyme activities of phosphoglucomutase (Pgm) and galactose-1-phosphate uridyl transferase (Gal7) were assayed at 30° C. by following the NADPH production at 340 nm using a spectrophotometer (HP 8353 UV-VIS system with Chemstation software from Hewlett Packard). Pgm and Gal7 activities were determined as earlier described (Bergmeyer et al., 1983; Elsevier et al., 1996) respectively, in a 1 ml reaction mixture activity at a minimum of two different concentrations of cell free extract. Galactokinase (Gal1) activity was measured with a method modified from (Mizoguchi et al., 1993). The reaction mixture contained: 0.1 M phosphate buffer (pH 7.5); 3.0 mM $MgCl_2$; 1.8 mM NaF; 1.5 mM ATP and four different concentrations of cell free extract. After 5 minutes at 30° C. adding galactose to 2.5 mM started the reaction, and the reaction mixture was incubated for another 5 minutes and then boiled for 2 minutes. The amount of consumed galactose was determined by measuring the residual concentration of galactose enzymatically (Boehringer Mannheim kit 176303) after centrifugation (10 minutes, 1000 g). Protein content in cell free extracts was determined by the Lowry method (Lowry et al., 1951), using fatty-acid free BSA (Sigma A-6003) as standard.

The results of the in vitro enzyme activity measurements supported the conclusion from the transcription analysis. The results are shown in the table below.

| | In vitro Enzyme activity | |
|---|---|---|
| | Fold change[a] | |
| Enzyme | SO7 | SO16 |
| Gal7 | 1.6 | −1.3 |
| Gal10 | −1.2 | 1.2 |
| Gal5 | 2.6[b] | 1.5[b] |

[a]Fold change compared to wild type strain.
[b]Fold change of total phosphoglucomutase activity.

The in vitro enzyme activities of Gal1 and Ga7 did not change significantly in any of the two mutants compared with the reference strain, while the in vitro activity of Gal5 had increased 2.6 and 1.5 in SO7 and SO16 respectively.

EXAMPLE 6

Over Expression of PGM2

To test the new hypothesis that Gal5 does exert control over the flux through the galactose utilisation pathway we constructed a strain over expressing PGM2. S. cerevisiae was transformed with a multicopy expression vector from Masuda et al. (2001) containing PGM2 under the control of the strong PMA1 gene promoter. The S. cerevisiae strain with over expression of PGM2 was compared with the corresponding reference strain CEN.PK113-7D (WT) under controlled conditions in aerobic batch cultivations on a minimal media with a start concentration of 15 g/l galactose. Cultivations of both strains were done in triplicates. The batch cultivations were carried out as described in Example 2.

Results from the batch cultivation with the PGM2 strain are shown in FIG. 4 and overall results from batch cultivations of the strain and the WT are shown in the table below. Data is given as the average of three similar independent cultivations ± the standard deviation.

| | WT | PGM2 strain |
|---|---|---|
| Specific growth rate ($h^{-1}$) | 0.17 ± 0.01 | 0.23 ± 0.02 |
| Specific galactose uptake rate (g galactose/g DW/h) | 0.60 ± 0.03 | 1.04 ± 0.07 |
| Specific ethanol production rate (g ethanol/g DW/h) | 0.11 ± 0.01 | 0.30 ± 0.03 |
| Yield of biomass on galactose (g DW/g galactose) | 0.22 ± 0.01 | 0.22 ± 0.01 |

The resulting PGM2 strain had a significantly increased maximum specific galactose uptake rate compared to the both the reference strain and the two other mutants. Overexpressing PGM2 resulted in a 70% increase in the maximum specific galactose uptake rate and a 3 times higher maximum specific ethanol production rate compared to the wild type strain showing that Gal5 is rate controlling for galactose utilisation. The maximum specific growth rate of the PGM2 strain was not negatively affected, but rather increased. In vitro enzyme activity measurements verified that the concentration of active phosphoglucomutase had indeed increased in the PGM2 strain, showing 17-fold higher phosphoglucomutase activity. However, the in vitro enzyme activity of Gal7 had also increased with approximately 3 fold in the PGM2 strain. This might have a positive effect on the galactose utilisation rate as well.

REFERENCES

Bergmeyer H U, Bergmeyer J, and Grassl M. (1983) Methods of enzymatic analysis. Volume II. Samples, reagents, assessment of results. Verlag Chemie, Weinheim Daugherty, J. P., Kraemer, W. F., & Joshi, J. G. (1975) Purification and properties of phosphoglucomutase from Fleischmann's yeast. Eur. J Biochem. 57, 115-126.

van Dijken, J. P., Bauer, J., Brambilla, L., Duboc, P., Francois, J. M., Gancedo, C., Giuseppin, M. L. F., Heinen, J. J., Hoare, M., Lange, H. C., Madden, E. A., Niederberger, P., Nielsen, J., Parrou, J. L., Petit, T., Porro, D., Reuss, M., van Riel, N., Rizzi, M., Steensma, H. Y., Verrips, C. T., Vindelov, J., & Pronk, J. T. (2000) Enz. Microb. Technol. 26, 706-714

Elsevier J P, Wells L, Quimby B B, and Fridovich-Keil J L. (1996) Heterodimer formation and activity in the human enzyme galactose-1-phosphate uridylyltransferase. Proc. Natl. Acad. Sci. USA 93: 7166-7171.

Frovola, E., Johnston, M., Majors, J. (1999) Binding of glucose-dependent Mig1p repressor to the GAL1 and GAL4 promoters in vivo: regulation by glucose and chromatin structure. Nucleic Acid Res. 27:1350-1358

Ideker, T. et al. Integrated genomic and proteomic analyses of a systematically perturbed metabolic network. Science 292, 929-934 (2001).

Johnston, M. (1987) A model fungal gene regulatory mechanism: the GAL genes of Saccharomyces cerevisiae. Microbiol. Rev. 51:458-476

Johnston, M. & Carlson, M. (1992) Regulation of carbon and phosphate utilization. Pp. 193-281. In: "The Molecular and Cellular Biology of the yeast *Saccharomyces*: Gene Expression". Jones, E. W., Pringel, J. R., Broach, J. (eds.) Cold Spring Harbor Laboratory Press, Cold Spring Harbor, N.Y.

Keleher, C. A., Redd, M. J., Schultz, J., Carlson, M., Johnston, A. D. (1992) Ssn6-Tup1 is a general repressor of transcription in yeast. *Cell* 68:709-719

Klein, C. J. L., Olsson, L., Nielsen, J. (1998) Glucose control in *Saccharomyces cerevisiae*: the role of MIG1 in metabolic functions. *Microbiol*. 144

Lowry, O. H., Rosebrough, N. J., Farr, A. L., & Randall, R. J. (1951) Protein measurement with the folin phenol reagent. *J. Biol. Chem.* 193, 265-275.

Masuda, C. A., Xavier, M. A., Mattos, K. A., Galina, A., & Montero-Lomeli, M. Phosphoglucomutase is an in vivo lithium target in yeast. *J. Biol. Chem* 276, 37794-37801 (2001).

Melcher, K. (1997) in Yeast sugar metabolism: Biochemistry, genetics, biotechnology, and applications. eds. Zimmermann, F K & Entian, K. D. 235-269, Technomic Publishing Company, Inc., Lancaster.

Mizoguchi N, Eguchi T, Sakura N, and Ueda K. (1993) Erythrocyte galactokinase assay with high performance liquid chromatography. *Clin. Chim. Acta* 216: 145-151.

Møller, K., Bro, C., Piskur, J., Nielsen, J., & Olsson, L. (2002) Steady state and transient-state analysis of aerobic fermentation in *Saccharomyces kluyveri*. *FEMS Yeast Res.* 2, 233-244.

Nielsen, J. Metabolic engineering. *Appl. Microbiol. Biotechnol.* 55, 263-283 (2001).

Oh, D. & Hopper, J. E. (1990) Transcription of a yeast phosphoglucomutase isozyme gene is galactose inducible and glucose repressible. *Mol. Cell Biol.* 10, 1415-1422

Ostergaard, S., Olsson, L., Johnston, M., & Nielsen, J. (2000) Increasing galactose consumption by *Saccharomyces cerevisiae* through metabolic engineering of the GAL gene regulatory network. *Nat. Biotechnol.* 18, 1283-1286.

Platt, A. & Reece, R. J. (1998) The yeast galactose genetic switch is mediated by the formation of a Gal4p-Gal80p-Gal3p complex. *EMBO J.* 17:4086-4091

Purnelle, B., Skala, J., van Dyck, L., & Goffeau, A. (1994) Analysis of an 11.7 kb DNA fragment of chromosome XI reveals a new tRNA gene and four new open reading frames including a leucine zipper protein and a homologue to the yeast mitochondrial regulator ABF2. *Yeast* 10, 125-130.

Treitel, M. A. & Carlson, M. (1995) Repression by SSN6-TUP1 is directed by MIG1, a repressor/activator protein. *Proc. Nat. Acad. Sci. USA* 92:3132-3136

Verduyn, C., Postma, E., Scheffers, W. A. & van Dijken, J. P. (1992) Effect of benzoic acid on metabolic fluxes in yeasts: a continuous-culture study on the regulation of respiration and alcoholic fermentation. *Yeast* 8, 501-517.

Wieczorke, R. et al. (1999) Concurrent knock-out of at least 20 transporter genes is required to block uptake of hexoses in *Saccharomyces cerevisiae*. *FEBS Lett.* 464, 123-128.

Zheng, W., Xu, H. E., & Johnston, S. A. (1997) The cysteine-peptidase bleomycin hydrolase is a member of the galactose regulon in yeast. *J. Biol. Chem* 272, 30350-30355.

Zhu, H. et al. Global analysis of protein activities using proteome chips. *Science* 293, 2101-2105 (2001).

Zubay, G. (1998) Biochemistry, 2. ed., Macmillan Publishing Company, New York

The invention claimed is:

1. A recombinant, prototrophic micro-organism exhibiting an increased level of galactose uptake rate when cultured on a nutrient source providing galactose, said micro-organism being a *Saccaromyces cerevisiae* having the ability to grow on minimal medium and over expressing PGM2, which is an enzyme catalysing the conversion of glucose-1 phosphate to glucose-6 phosphate in the galactose uptake and metabolism pathway, compared to a reference micro-organism having a native level of expression of said enzyme and from which the recombinant micro-organism is derived, wherein said over expression of said enzyme is due to said micro-organism having multiple copies of a gene coding for said enzyme or is due to a gene coding for said enzyme being under the control of a genetic control sequence which has been recombinantly introduced and which is not natively associated with said gene.

2. The micro-organism of claim 1, wherein said enzyme is expressed in the micro-organism at a level which is 1.5 or more times that of said reference micro-organism.

3. The micro-organism of claim 1, having multiple copies of a gene coding for said enzyme.

4. The micro-organism of claim 1, wherein a gene coding for said enzyme is under the control of a genetic control sequence which has been recombinantly introduced and which is not natively associated with said gene, leading to over expression of said enzyme.

5. The micro-organism of claim 1, which exhibits an increase of maximum specific galactose uptake rate of at least 10% in comparison to the maximum specific galactose uptake rate in said reference micro-organism.

6. The micro-organism of claim 1, which exhibits an increase of said enzyme expression of at least 2 fold in comparison to the enzyme expression in said reference micro-organism.

7. The micro-organism of claim 1, which exhibits an increased maximum specific ethanol production rate compared to the maximum specific ethanol production rate in said reference micro-organism.

8. The micro-organism of claim 6, wherein said specific ethanol production rate is increased by at least a factor of 1.5 relative to the rate in said reference microorganism.

9. A method of ethanol production, lactic acid production, or citric acid production, comprising growing a micro-organism on a galactose containing nutrient source to produce ethanol as a metabolite, wherein said micro-organism is a recombinant, prototrophic micro-organism according to claim 1, and recovering ethanol, lactic acid, or citric acid therefrom.

10. The method of claim 9, wherein said enzyme activity is expressed in the micro-organism at a level which is 1.5 or more times the level of said enzyme activity in said reference micro-organism.

11. The method of claim 9, wherein the micro-organism exhibits an increase of maximum specific galactose uptake rate of at least 10% in comparison to said reference micro-organism.

12. The method of claim 9, wherein the micro-organism exhibits an increase of said enzyme activity of at least 2 fold in comparison to said enzyme activity in said reference micro-organism.

13. The method of claim 9, wherein the micro-organism exhibits an increased maximum specific ethanol production rate compared to said rate in said reference micro-organism.

14. The method of claim 13, wherein said ethanol production rate is increased by at least a factor of 1.5.

15. The method of claim 9, wherein said nutrient source comprises lactose or raffinose.

* * * * *